United States Patent [19]

Cortese et al.

[11] 4,327,725
[45] May 4, 1982

[54] OSMOTIC DEVICE WITH HYDROGEL DRIVING MEMBER

[75] Inventors: Richard Cortese, San Jose; Felix Theeuwes, Los Altos, both of Calif.

[73] Assignee: ALZA Corporation, Palo Alto, Calif.

[21] Appl. No.: 210,176

[22] Filed: Nov. 25, 1980

[51] Int. Cl.³ .............................................. A61M 7/00
[52] U.S. Cl. ................................................... 128/260
[58] Field of Search ..................... 128/260; 424/19, 21

[56] References Cited

U.S. PATENT DOCUMENTS

| | | | |
|---|---|---|---|
| 4,111,201 | 9/1978 | Theeuwes | 128/260 |
| 4,111,202 | 9/1978 | Theeuwes | 128/260 |
| 4,111,203 | 9/1978 | Theeuwes | 128/260 |
| 4,203,439 | 5/1980 | Theeuwes | 128/260 |
| 4,203,440 | 5/1980 | Theeuwes | 128/260 |

*Primary Examiner*—C. Fred Rosenbaum
*Attorney, Agent, or Firm*—Paul L. Sabatine; Edward L. Mandell

[57] ABSTRACT

An osmotic device is disclosed comprising a semipermeable wall surrounding a compartment housing an agent that is insoluble to very soluble in aqueous and biological fluids, and a layer of a fluid swellable, hydrogel. A passageway in the wall connects the agent with the exterior of the device.

40 Claims, 10 Drawing Figures

OSMOTIC DEVICE WITH HYDROGEL DRIVING MEMBER

FIELD OF THE INVENTION

This invention pertains to an osmotic device. More particularly, the invention relates to an osmotic device comprising a semipermeable wall surrounding a compartment containing a beneficial agent that is insoluble to very soluble in an aqueous fluid, and a layer of a water-swellable cross-linked hydrogel driving member. A passageway through the wall connects the exterior of the device with the agent for delivering the agent from the device.

BACKGROUND OF THE INVENTION

Osmotic devices for delivering beneficial agents to environments of use are known to the prior art in U.S. Pat. No. 3,845,770 issued to Felix Theeuwes and Takeru Higuchi, and in U.S. Pat. No. 3,916,899, issued to the same patentees. The osmotic devices disclosed in those patents comprise a semipermeable wall that surrounds a compartment containing an agent. The wall is permeable to the passage of an external fluid, and substantially impermeable to the passage of agent. There is a passageway through the wall for delivering the agent from the device. These devices release agent by fluid being imbibed through the wall into the compartment at a rate determined by the permeability of the wall and the osmotic pressure gradient across the wall to produce an aqueous solution containing agent that is dispensed through the passageway from the device. These devices are extraordinarily effective for delivering an agent that is soluble in the fluid and exhibits an osmotic pressure gradient across the wall against the fluid, and for delivering an agent that has limited solubility in the fluid and is admixed with an osmotically effective compound that is soluble in the fluid and exhibits an osmotic pressure gradient across the wall against the fluid.

A pioneer advancement in osmotic delivery devices was presented to the art by inventor Felix Theeuwes in U.S. Pat. No. 4,111,202. In this patent, the delivery kinetics of the device is enhanced, for delivering agents with degrees of solubility in aqueous fluids that are difficult to deliver, such as very soluble or insoluble in the fluid, by manufacturing the device with an agent compartment and an osmagent compartment separated by a film, which film is movable from a rested to an expanded state. The device delivers agent by fluid being imbibed through the wall into the osmagent compartment producing a solution that causes the compartment to increase in volume and act as a driving force that is applied against the film. This force urges the film to expand against the agent compartment and correspondingly diminish the volume of this compartment, whereby agent is dispensed through the passageway from the device. While this device operates successfully for its intended use, and while it can deliver numerous difficult to deliver agents, its use can be limited because of the manufacturing steps needed for fabricating and placing the movable film in the device. It will be appreciated by those versed in the art, that if a device can be provided without the movable film, and have a compartment containing an agent and an expandable driving member, such as a layer of a swellable hydrogel, that can generate a force for delivering the agent, and can be manufactured free of the tribulations known to the art, such a device would have a positive value and represent an advancement in the delivery arts.

OBJECTS OF THE INVENTION

Accordingly, it is an immediate object of this invention to provide an osmotic device for the controlled delivery of a beneficial agent, and which device represents a further improvement and advancement in the delivery arts.

Yet another object of the invention is to provide an osmotic device that is useful for delivering agents that are difficult to deliver and can be delivered by the subject device at meaningful rates over time.

Still another object of the invention is to provide an osmotic device having a compartment containing an agent that can be from insoluble to very soluble in an aqueous fluid, and an expandable driving member consisting of a layer of hydrogel, which hydrogel operates to diminish the volume occupied by the agent, thereby delivering the agent from the device at a controlled rate over time.

Yet another object of the invention is to provide an osmotic device having a compartment housing an agent that can be from insoluble to very soluble in an aqueous fluid, and an expandable driving member made of a hydrogel, and which hydrogel can generate a force that acts to diminish the volume occupied by the agent, thereby maintaining the agent in a saturated state during its release from the device.

Still another object of the invention is to provide an osmotic device comprising a compartment housing a layer of an agent and a layer of an expandable driving member formed of a hydrogel, which hydrogel can continuously increase its volume while correspondingly decreasing the volume initially occupied by the agent for maintaining excess solid agent in the compartment over an increased length of time.

Yet still a further object of this invention is to provide an osmotic device that can continuously maintain substantially the major amount of an agent present as a saturated solution throughout its release from the device.

Still a further object of the invention is to provide an osmotic therapeutic device that can administer a complete pharmaceutical regimen comprising very soluble, or poorly soluble agents, at a controlled and continuous rate to a human, for a particular time period, the use of which requires intervention only for initiation and possibly termination of the regimen.

Other objects, features, aspects and advantages of the invention will be more apparent to those versed in the art from the following detailed specification taken in conjunction with the figures and the accompanying claims.

SUMMARY OF THE INVENTION

This invention concerns an osmotic device for dispensing an active agent to an environment of use. The device comprises a semipermeable wall surrounding a compartment that communicates with the exterior of the device through a passageway in the wall. The compartment contains an active agent exhibiting degrees of solubility in an aqueous fluid, for example, an agent that is soluble in an exterior fluid and exhibits an osmotic pressure gradient across the wall against the fluid, or it contains an agent having limited solubility in the fluid that exhibits a limited pressure gradient across the wall against the fluid. In either instance, the agent is next to the passageway. The compartment also contains a layer of an expandable driving member formed of a water-swellable hydrogel that absorbs fluid imbibed into the compartment, and can expand from a rested to an expanded state. The hydrogel is in contact with the agent and positioned distant form the passageway. Agent is released from the device by the combined actions of fluid being imbibed through the wall into the compartment producing a solution or suspension containing agent, and by fluid being imbibed by the hydrogel causing it to expand and increase in volume, thereby exerting a force against the solution or suspension that decreases their respective volume, whereby the agent is released through the passageway at a rate controlled by the permeability of the wall, the osmotic pressure gradient across the wall, and the rate of expansion of the driving hydrogel over a prolonged period of time.

BRIEF DESCRIPTION OF DRAWINGS

In the drawings, which are not drawn to scale, but are set forth to illustrate various embodiments of the invention, the figures are as follows.

In the drawings and the specification, like parts in related figures are identified by like parts. The terms appearing earlier in the specification and in the description of the drawings, as well as embodiments thereof, are further detailed elsewhere in the disclosure.

DETAILED DESCRIPTION OF THE DRAWINGS

Turning now to the drawings in detail, which are examples of various osmotic delivery devices provided by the invention, and which examples are not to be construed as limiting, one example of an osmotic device is seen in FIGS. 1A through 1E, considered together, and indicated by the numeral 10. In FIGS. 1A through 1E, device 10 is seen comprised of a body member 11 having a wall 12 that surrounds and forms a compartment 13, as seen in opened device 10 in FIGS. 1B through 1E. Compartment 13, comprises a layer of a beneficial agent that can be from insoluble to very soluble in an aqueous fluid and is identified by dots 14, which agent when soluble in the fluid exhibits an osmotic pressure gradient across wall 12 against an exterior fluid, indicated by dashes 15, that is imbibed into compartment 13. Compartment 13 in another embodiment contains a layer of agent 14 that has limited solubility or is substantially insoluble in fluid 15, and it exhibits a limited, or it may not exhibit any osmotic pressure gradient across wall 12 against the exterior fluid. When agent 14 has a limited solubility, or if it is substantially insoluble in fluid 15, it can be mixed with an osmagent that is soluble in the external fluid and exhibits an osmotic pressure gradient across wall 12 against the fluid. Wall 12 is formed of a polymeric material that is substantially permeable to the passage of the external fluid, and it is substantially impermeable to the passage of agent and osmagent. The semipermeable polymer forming wall 12 is non-toxic and it maintains its physical and chemical integrity during the life of device 10.

Compartment 13 further houses a layer of an expandable driving member made from a hydrogel and identified by wavy lines 16. Hydrogel 16 is a hydrophilic, water insoluble polymer, optionally cross-linked, which possesses osmotic properties such as the ability to imbibe external fluid and exhibit an osmotic pressure gradient across the semipermeable wall against the fluid. Hydrogel 16 absorbs fluid imbibed into the compartment and swells or expands to some equilibrium state. At equilibrium the osmotic pressure of the hydrogel approximately equals the swelling pressure of the hydrogel, and the osmotic pressure of the hydrogel network is the driving force of the swelling, expanding member 16. Hydrogel 16 is in contact with agent 14 and at the interface formed by the hydrogel and the agent, of the agent and an osmagent, a thin precipitate 18 forms in the outer surface of hydrogel 16. The precipitate forms in the presence of a solution containing the agent, or the agent and an osmagent, and it is substantially imprevious and restricts the passage of agent 14 into hydrogel 16. The precipitate further serves as an in situ formed membrane integral with the hydrogel for applying pressure against agent 14 during operation of device 10.

Device 10 releases agent 14 through a passageway 17 in wall 12 that communicates agent 14 with the exterior of device 10. Device 10 releases agent 14 by fluid being imbibed into compartment 13 in a tendency towards osmotic equilibrium at a rate determined by the permeability of wall 12 and the osmotic pressure gradient across wall 12. The imbibed fluid continuously forms a solution containing agent, or a solution of osmagent containing agent, in suspension which solution in either instance is released by the combined operation of device 10. These operations include the solution being osmotically delivered through passageway 17 due to the continuous formation of solution in the compartment, and by the hydrogel swelling and increasing in volume and applying pressure against the solution thereby delivering it to the exterior of device 10.

Compartment 13 operates to substantially insure that delivery of agent 14 from compartment 13 is constant over a prolonged period of time by two methods. First, hydrogel 16 operates to continuously concentrate agent 14 by imbibing some fluid from agent 14 to keep the concentration of agent 14 from falling below saturation. Secondly, hydrogel 16 by imbibing external fluid 15 across wall 12 continuously increases its volume, as illustrated by the expansion of hydrogel 16 in FIGS. 1C through 1E, thereby exerting a force on agent 14 and diminish the volume of agent 14, thusly concentrating agent 14 in compartment 13. The swelling and expansion of hydrogel 16, with its accompanying increase in volume, along with the simultaneous, corresponding reduction in volume of agent 14, assures the delivery of agent 14 at a controlled rate over time.

Device 10 of FIGS. 1A through 1E can be made into many embodiments including the presently preferred embodiments for oral use, that is, for releasing either a locally or systemically acting therapeutic agent in the gastrointestinal tract over time. Oral system 10 can have various conventional shapes and sizes such as round with a diameter of 3/16 inches to ½ inch, or it can be shaped like a capsule having a range of sizes from triple zero to zero, and from 1 to 8. In these forms, system 10 can be adapted for administering agent to numerous animals, warm blooded mammals, humans, avians, reptiles and fishes.

Figure 1A:
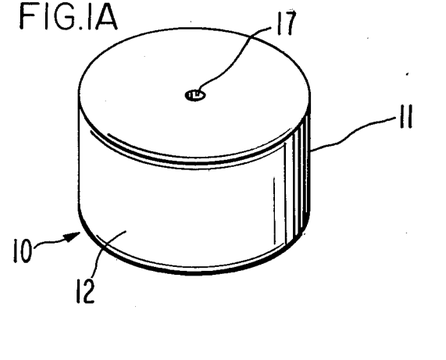
FIG. 1A is an isometric view of an osmotic device designed for orally administering a beneficial agent to the gastrointestional tract.
Figure 1B:
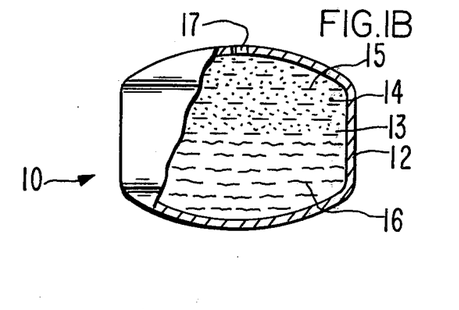
FIG. 1B is an opened view of the osmotic device of FIG. 1A illustrating the internal structure of the device of FIG. 1A.
Figure 1C:
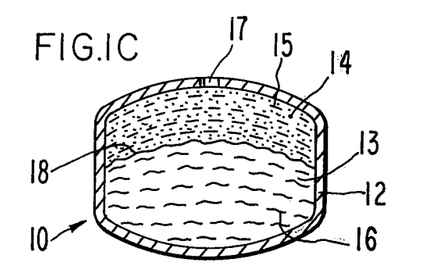
FIGS. 1C through 1E are seen in opened section illustrating the osmotic device of FIGS. 1A and 1B in operation and delivering the beneficial agent from the device.
Figure 1D:
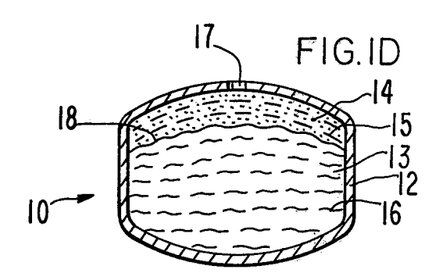
Figure 1E:
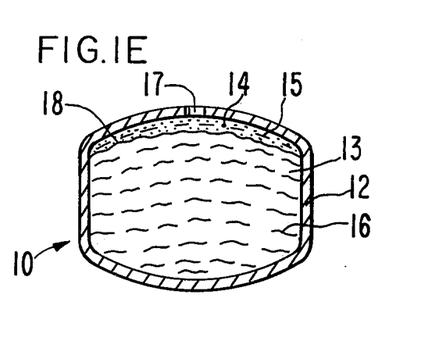
Figure 2:
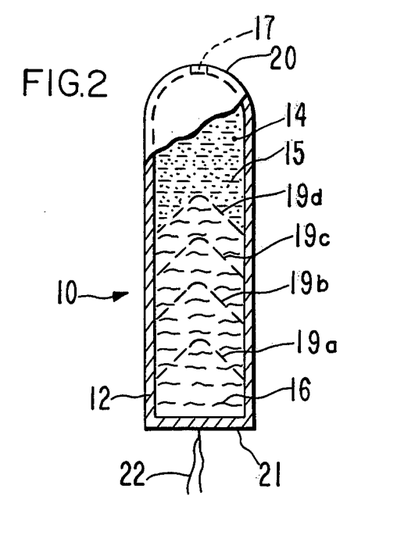
FIG. 2 shows an osmotic therapeutic device, with its wall partially broken away, designed for delivering a beneficial agent into a body passageway, such as the ano-rectal and vaginal passageways.

FIG. 2 shows another embodiment, an osmotic device 10 designed for placement in a body passageway, such as a vagina, or the ano-rectal canal. Device 10 has an elongated, cylindrical, self-sustaining shape with a rounded lead end 20, a trailing end 21, and it is equipped with a manually controlled string for easily removing device 10 from a passageway. Device 10 of FIG. 2 is structurally identical with device 10 as described above, and it has a hydrogel area 16 that operates in a like manner by being capable of expanding from 19a through 19d. Device 10 of FIG. 2 in one embodiment contains an agent, that is, a drug 14 designed for absorption by the vaginal mucosa, or the ano-rectal mucosa, to produce a local or systemic effect over a prolonged period of time.

Figure 3:
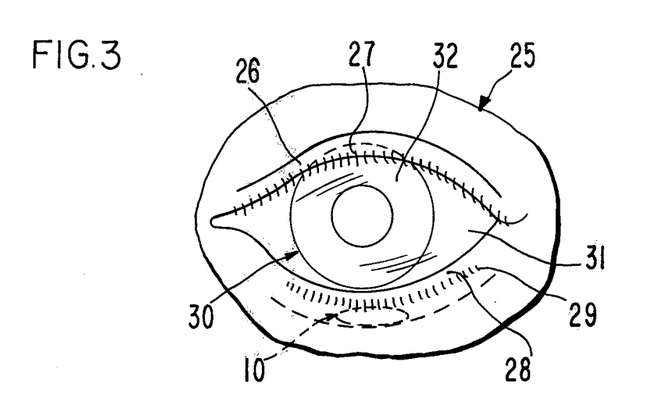
FIG. 3 is a front view of a human eye illustrating an osmotic therapeutic ocular insert in operative position in a biological environment of use.

Referring to FIG. 3, an osmotic device manufactured as an ocular therapeutic insert 10 is seen in an eye 25 for administering a drug at an osmotically metered dosage rate thereto. In FIG. 3, eye 25 is comprised of an upper eyelid 26 with eyelashes 27 and lower eyelids 28 with eyelashes 29. Eye 25 anatomically is comprised of an eyeball 30 covered for the greater part by sclera 31 and at its center area by cornea 32. Eyelids 26 and 28 are lined with an epithelial membrane or palpebral conjunctiva, and sclera 31 is lined with a bulbar conjunctiva that covers the exposed surface of eyeball 30. Cornea 30 is covered with a transparent epithelial membrane. The portion of the palpebral conjunctiva which lines upper eyelid 26 and the underlying portion of the bulbar conjunctiva define an upper cul-de-sac, while that portion of the palpebral conjunctiva which lines lower eyelid 28 and the underlying portion of the bulbar conjunctiva define a lower cul-de-sac. Osmotic insert 10, seen in broken lines, is designed for placement in the upper or lower cul-de-sac. Insert 10 is seen in the lower cul-de-sac and it is held in place by the natural pressure of lower eyelid 28. Insert 10 contains an ophthalmic drug for release to eye 25 at a controlled and continuous rate over a prolonged period of time.

Ocular insert 10, manufactured according to the inventive principles described supra, can have any geometric shape that fits comfortably in the cul-de-sac. Typical shapes include ellipsoid, bean, banana, circular, ring, rod, rectangular, doughnut, crescent, and half-ring shaped inserts. In cross-section, the insert can be doubly convex, concavo-convex, rectangular and the like, as the device in use will tend to conform to the shape of the eye. The dimensions of an ocular insert can vary widely with the lower limits governed by the amount of drug to be administered to the eye as well as the smallest sized insert that can be placed in the eye. The upper limits on the size of the insert is governed by the space limitation in the eye consistent with comfortable retention in the eye. Satisfactory inserts have a length of 4 to 20 millimeters, a width of 1 to 15 millimeters, and a thickness of 1 to 4 millimeters. The ocular insert can contain from 0.15 micrograms to 250 milligrams of drug, or more, for release over time.

While FIG. 1 through 3 are illustrative of various devices that can be made according to the invention, it is to be understood these devices are not to be construed as limited, as the devices can take a wide variety of shapes, sizes and forms for delivering agent to the environment of use. For example, the devices include buccal, implant, artificial gland, cervical, intrauterine, ear, nose, dermal, subcutaneous and blood delivery inserts. The devices also can be sized, shaped, structured and adapted for delivering an active agent in streams, aquariums, fields, factories, reservoirs, laboratory facilities, hot houses, transportation mean, naval means, military means, hopitals, veterinary clinics, nursing homes, farms, zoos, sickrooms, chemical reactions, and other environments of use.

DETAILED DESCRIPTION OF THE INVENTION

In accordance with the practice of the invention, it has now been found that osmotic delivery device 10 can be manufactured with a wall 12 formed of a material that does not adversely affect the agent 14, which includes drug, an osmagent, an animal, or other host, and it is permeable to the passage of an external aqueous type fluid 15, such as water and biological fluids, while remaining essentially impermeable to the passage of agents, including drugs, osmagents, and the like. The selectively, semipermeable materials forming wall 12 are insoluble in fluids, and they are non-erodible, or they can be made to bioerode after a predetermined period with bioerosion corresponding to the end of the agent release period. Typical materials for forming wall 12 include semipermeable polymers known to the art as osmosis and reverse osmosis membranes, such as cellulose acylate, cellulose diacylate, cellulose triacylate, cellulose acetate, cellulose diacetate, cellulose triacetate, agar acetate, amylose triacetate, beta glucan acetate, acetaldehyde dimethyl acetate, cellulose acetate ethyl carbamate, polyamides, polyurethanes, sulfonated polystyrenes, cellulose acetate phthalate, cellulose acetate methyl carbamate, cellulose acetate succinate, cellulose acetate dimethylaminoacetate, cellulose acetate ethyl carbamate, cellulose acetate chloroacetate, cellulose dipalmatate, cellulose dioctanoate, cellulose dicaprylate, cellulose dipentanlate, cellulose acetate valerate, cellulose acetate succinate, cellulose propionate succinate, methyl cellulose, cellulose acetate p-toluene sulfonate, cellulose acetate butyrate, cross-linked selectively semipermeable polymers formed by the coprecipitation of a polyanion and a polycation as disclosed in U.S. Pat. Nos. 3,173,876; 3,276,586; 3,541,005; 3,541,006; and 3,546,142, semipermeable polymers as disclosed by Loeb and Sourirajan in U.S. Pat. No. 3,133,132, lightly cross-linked polystyrene derivatives, cross-linked poly(sodium styrene sulfonate), poly(vinylbenzyltrimethyl ammonium chloride), cellulose acetate having a degree of substitution up to 1 and an acetyl content up to 21%, cellulose diacetate having a degree of substitution of 1 to 2 and an acetyl content of 21 to 35%, cellulose triacetate having a degree of substitution of 2 to 3 and an acetyl content of 35 to 44.8%, as disclosed in U.S. Pat. No. 4,160,020. Generally, semipermeable materials useful for forming wall 12 will have a fluid permeability of $10^{-5}$ to $10^{-1}$ (cc·mil/cm²·hr·atm) expressed per atmosphere of hydrostatic or osmotic pressure difference across semipermeable wall 12 can be used for the intended purpose.

The expressions active agent, as used herein includes any beneficial agent or compound, that can be delivered from the device to produce a beneficial and useful result. The agent can be insoluble to a very soluble in the exterior fluid. For example, the agent can be very soluble in fluid 15 that enters compartment 13 and function as its own osmotically effective solute, or it can be poorly soluble in the fluid and be mixed with an osmotically effective compound that is soluble in the fluid for delivering an agent from the device. The term active agent includes pesticides, herbicides, germicides, biocides, algicides, rodenticides, fungicides, insecticides, anti-oxidants, plant growth promoters, plant growth inhibitors, preservatives, disinfectants, sterilization agents, catalysts, chemical reactants, fermetation agents, sex sterilants, fertility inhibitors, fertility promoters, air purifiers, micro-organism attenuators, and other agents that benefit the environment of use.

In the specification and the accompanying claims, the term agent includes drug, and the term drug includes any physiologically or pharmacologically active substance that produces a local or systemic effect, in animals, including warm blooded mammals, humans and primates, avians, household, sport an farm animals, laboratory animals, fishes, reptiles and zoo animals. The term physiologically as used herein denotes the administration of a drug to produce normal levels and functions. The term pharmacologically denotes variations in response to amount of drug administered to the host. *Stedman's Medical Dictionary,* 1966, published by Williams and Wilkins, Baltimore, MD. The active drug that can be delivered includes inorganic and organic drugs without limitations, those drugs that act on the central nervous system, depressants, hypnotics, sedatives, psychic energizers, tranquilizers, anticonvulsants, muscle relaxants, antiparkinson agents, analgesics, anti-inflammatory, local anesethetics, muscle contractants, anti-microbials, anti-malarials, hormonal agents, contraceptives, sympathomimetics, diuretics, anti-parasitics, neoplastics, hypoglycemics, ophthalmics, electrolytes, diagnostic agents, and cardiovascular drugs.

Exemplary drugs that are or very soluble in water and can be delivered by the devices of this invention include prochlorperazine edisylate, ferrous sulfate, aminocaproic acid, potassium chloride, mecamylamine hydrochloride, procainamide hydrochloride, amphetamine sulfate, benzphetamine hydrochloride, isoproternol sulfate, methamphetamine hydrochloride, phenmetrazine hydrochloride, bethanechol chloride, methacholine chloride, pilocarpine hydrochloride, atropine sulfate, methascopolamine bromide, isopramide iodide, tridihexethyl chloride, phenformin hydrochloride, methylphenidate hydrochloride, oxprenolol hydrochloride, metoprolol tartrate, cimetidine hydrochloride, and the like.

Exemplary drugs that are poorly soluble in water and that can be delivered by the devices of this invention include diphenidol, meclizine hydrochloride, prochlorperazine maleate, phenoxybenzamine, thiethylperazine maleate, anisindone, diphenadione erythrityl tetranitrate, dizoxin, isofurophate, reserpine, acetazolamide, methazolamide, bendroflumethiazide, chlorpropamide, tolazamide, chlormadinone acetate, phenaglycodol, allopurinol, aluminum aspirin, methotrexate, acetyl sulfisoxazole, erythromycin, progestins, esterogenic progestational, corticosteriods, hydrocortisone, hydrocorticosterone acetate, cortisone acetate, triamcinolone, methyltesterone, 17$\beta$-estradiol, ethinyl estradiol, ethinyl estradiol 3-methyl ether, prednisolone, 17$\beta$-hydroxyprogesterone acetate, 19-nor-progesterone, norgestrel, norethindone, norethiderone, progesterone, norgesterone, norethynodrel, and the like.

Examples of other drugs that can be delivered by the osmotic device include aspirin, indomethacin, naproxen, fenoprofen, sulidac, diclofenac, indoprofen, nitroglycerin, propranolol, metoprolol, valproate, oxprenolol, timolol, atenolol, alprenolol, cimetidine, clonidine, imipramine, levodopa, chloropromazine, reserpine, methyl-dopa, dihydroxyphenylalanine, pivaloyloxyethyl ester of $\alpha$-methyldopa hydrochloride, theophylline, calcium gluconate, ferrous lactate, vincamine, diazepam, phenoxybenzamine, $\alpha$-blocking agents and the like. The beneficial drugs are known to the art in *Pharmaceutical Sciences,* by Remington 14th Ed., 1979, published by Mack Publishing Co., Easton, Penna.; *The Drug, The Nurse, The Patient, Including Current Drug Handbook,* 1974–1976, by Falconer, et al., published by Saunder Company, Philadelphia, Penna.; and *Medicinal Chemistry,* 3rd Ed., Vol. 1 and 2, by Burger, published by Wiley-Interscience, New York.

The drug can be in various forms, such as uncharged molecules, molecular complexes, pharmacologically acceptable salts such as hydrochlorides, hydrobromides, sulfate, laurylate, palmitate, phosphate, nitrite, borate, acetate, maleate, tartrate, oleate, and salicylate. For acid drugs, salts of metals, amines or organic cations, for example quaternary ammonium can be used. Derivatives of drugs such as esters, ethers and amides can be used. Also, a drug that is water insoluble can be used in a form that is a water soluble derivative thereof to serve as a solute, and on its release from the device, is converted by enzymes, hydrolyzed by body pH or other metabolic processes to the original biologically active form. The agent including drug, can be present in the compartment with a binder, dispersant, wetting agent, suspending agent, lubricant and dye. Representative of these include suspending agents such as acacia, agar, calcium carrageenan, alginic acid, algin, agarose powder, collagen, colloidal magnesium silicate, collidal silicon dioxide, hydroxyethyl cellulose, pectin, gelatin and calcium silicate; binders like polyvinyl pyrrolidone, and magnesium stearate, wetting agents such as fatty amines, fatty quaternary ammonium salts, and the like. The phrase drug formulation indicates the drug is present in the compartment accompanied by an osmagent, a binder, dye on the like.

The amount of agent present in the device is initially in excess of the amount that can be dissolved in the fluid that enters the device. Under this physical state, when the agent is in excess, the device will osmotically operate to give a substantially constant rate of release. Generally, the device can house from 0.05 ng to 5 g or more, with individual devices containing for example, 25 ng, 1 mg, 5 mg, 125 mg, 250 mg, 500 mg. 750 mg, 1.5 g, and the like. The devices can be administered once, twice or thrice daily.

The osmagent present in the device, when used according to the mode of the invention, are osmotically effective compounds soluble in fluid that enter the device, and exhibit an osmotic pressure gradient across the semipermeable wall against the exterior fluid. Osmotically effective osmagents useful for the present purpose include magnesium sulfate, magnesium chloride, sodium chloride, lithium chloride, potassium sulfate, sodium carbonate, sodium sulfite, lithium sulfate, potassium chloride, sodium sulfate, d-mannitol, urea, sorbitol inositol, raffinose, sucrose, glycose, mixtures thereof, and the like. The osmagent is usually present in an excess amount, and it can be in any physical forms, such as particle, powder, granule, and the like. The osmotic pressure in atmospheres, ATM, of the osmagents suitable for the invention will be greater than zero ATM, generally from zero ATM up to 500 ATM, or higher.

The hydrogel suitable for the purpose of the invention are swellable, hydrophilic polymers. The swellable, hydrophilic polymers are in one preferred embodiment lightly cross-linked, such cross-links being formed by covalent or ionic bond, which interact with water and aqueous biological fluids and swell or expand to some equilibrium state. The hydrogels exhibit the ability to swell in water and retain a significant fraction of water within its structure, and when cross-linked they will not dissolve in the water. The hydrogels can be of plant and animal origin, hydrogels prepared by modifying naturally occurring structures, and synthetic polymer hydrogels. The polymers swell or expand to a very high degree, usually exhibiting a 2 to 50 fold volume increase. Hydrophilic polymeric materials for the purpose include poly(hydroxyalkyl methacrylate), poly(N-vinyl-2-pyrrolidone), anionic and cationic hydrogels, polyelectrolyte complexes, poly(vinyl alcohol) having a low acetate residual and cross-linked with glyoxal, formaldehyde, or glutaraldehyde, methyl cellulose cross-linked with dialdehyde, a mixture of cross-linked agar and carboxymethyl cellulose, a water insoluble, water-swellable copolymer produced by forming a dispersion of finely divided copolymer of maleic anhydride with styrene, ethylene, propylene, butylene, or isobutylene cross-linked with from 0.001 to about 0.5 moles of a polyunsaturated cross-linking agent per mole of maleic anhydride in the copolymer, water-swellable polymers of N-vinyl lactams, cross-linked polyethylene oxides, and the like.

Other hydrogels include hydrogels exhibiting a cross-linking of 0.05 to 60%, hydrophilic hydrogels known as Carbopol ® acidic carboxy polymer, Cyanamer ® polyacrylamides, cross-linked water-swellable indene-maleic anhydride polymers, Good-rite ® polyacrylic acid, polyethyleneoxide, starch graft copolymers, Aqua-Keeps ® acrylate polymer, diester cross-linked polyglucan, and the like. The hydrogels are known to the prior art in U.S. Pat. No. 3,865,108 issued to Hartop; in U.S. Pat. No. 4,002,173 issued to Manning; in U.S. Pat. No. 4,207,893 issued to Michaels; and in *Handbook of Common Polymers* by Scott and Roff, published by the Chemical Rubber Company, Cleveland, Ohio.

The solubility of an agent in the fluid that enters the compartment can be determined by known techniques. One method consists of preparing a saturated solution comprising the fluid plus the agent as ascertained by analyzing the amount of agent present in a definite quantity of the fluid. A simple apparatus for this purpose consists of a test tube of medium size fastened upright in a water bath maintained at constant temperature and pressure, in which the fluid and agent are placed and stirred by a rotating glass spiral. After a given period of stirring, a weight of the fluid is analyzed and the stirring continued an additional period of time. If the analysis shows no increase of dissolved agent after successive periods of stirring, in the presence of excess solid agent in the fluid, the solution is saturated and the results are taken as the solubility of the product in the fluid. If the agent is soluble, an added osmotically effective compound optionally may not be needed, if the agent has limited solubility in the fluid, then an osmotically effective compound can be incorporated into the device. Numerous other methods are available for the determination of the solubility of an agent in a fluid. Typical methods used for the measurement of solubility are chemical and electrical conductivity. Details of various methods for determining solubilities are described in *United states Public Health Service Bulletin*, No. 67 of the Hygenic Laboratory; *Encyclopedia of Science and Technology*, Vol. 12, pages 542 to 556, 1971, published by McGraw-Hill, Inc.; and *Encyclopedia Dictionary of Physics*, Vol. 6, pages 547 to 557, 1962, published in Pergamon Press, Inc. For the purpose of the invention, the phrase agents with degrees of solubility as used herein indicates, agents that are insoluble to very soluble in aqueous and biological fluids. Further for this purpose, an insoluble agent indicates a solubility of less than 25 mg of agent in a ml of fluid, a poorly soluble agent is one that dissolves in the range of about 25 mg to 150 mg of agent per ml of fluid, a soluble agent dissolves about 150 mg to 600 mg of agent per ml of fluid, and a very soluble agent dissolves in excess of 600 mg of agent per ml of fluid. While the presently preferred embodiments have been described with reference to poorly or very soluble agents, it is to be understood the device can be used to deliver other agents.

Figure 4:
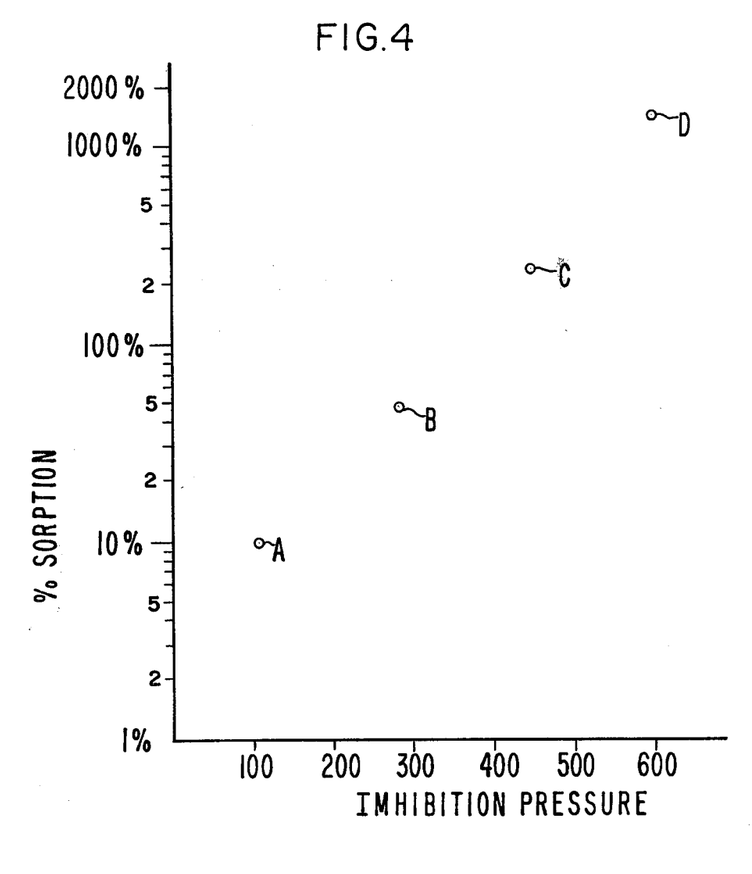
FIG. 4 is a graph depicting the precent weight uptake that polymers A, B, C, and D respectively exhibit in a saturated solution of sodium chloride in water as a function of their osmotic imbibition pressures.

The interaction at the hydrogel-water interface can be ascertained by placing a film formed of a hydrogel in contact with an aqueous solution containing an active agent, and sometimes an osmagent, and observing the modification of the hydrogel at the hydrogel-aqueous environment. Modification of the surface of the polymeric hydrogel, during operation of the device, in situ, leads to an in situ formed precipitate in its outer surface of the hydrogel, thereby indicating the hydrogel and the solution are suitable for operating in the compartment of the device. A representative procedure that can be used consists in measuring the percent weight gain for various polymers immersed in a saturated solution of a drug or an osmagent. The procedure broadly indicates interface absorption activity. That is, if there is little absorption by the polymer, there is correspondingly a little gain in weight and the polymer is suitable for the purpose. Similarly, if there is a large gain in weight indicating a large volume absorbed, the polymer is not preferred for the purpose. FIG. 4 represents the percent weight gain for 4 polymers immersed in a saturated solution of NaCl as a function of the imbibition pressure of the polymer. In FIG. 4, the polymers are as follows: A is Klucel H ® polymer; B is Polyox COAG ® polymer; C is Carbopol-934 ® polymer; and D is Na Carbopol-934 ® polymer. The samples were periodically removed from the solution, and the surface solution blotted and the polymer weighed. The equilibrium weight gain is defined as that point where no further increase in weight was measured over time.

Polymer imbibition pressure determination for a chosen polymer can be made by following the following procedure. A ½ inch round disc, fitted with a ½ inch diameter stainless steel plug, is charged with a known quantity of polymer with the plugs extending out either end. The plugs and the die were placed in a Carver press with plates between 200° and 300° F. A pressure of 10,000 to 15,000 PSI was applied to the plugs. After 10 to 20 minutes of heat and pressure the electrical heating to the plates were turned off, and tap water circulated through the plates. The resulting ½ inch discs were placed in an air suspension coater charged with 1.8 kg saccharide cores and coated with cellulose acetate having an acetyl content of 39.8% dissolved in 94:6 w/w, $CH_2Cl_2/CH_3OH$, to yield a 3% w/w solution. The coated systems were dried overnight at 50° C. The coated discs were immersed in water at 37° C. and periodically removed for a gravimetric determination of water imibed. The initial imbibition pressure was calculated by using the water transmission constant for the cellulose acetate, after normalizing imbibition values for membrane surface area and thickness. The polymer used in this determination was the sodium derivative of Carbopol-934 ® polymer, prepared according to the procedure of B. F. Goodrich Service Bulletin GC-36, "Carbopol ® Water-Soluble Resins," page 5, published by B. F. Goodrich, Akron, Ohio.

The cumulative weight gain values, y, as a function of time, t, for the water soluble polymer disc coated with the cellulose acetate were used to determine the equation of the line $y = c + bt + at^2$ passing through those points by a least square fitting technique.

The weight gain for the Na Carbopol-934 is given by equation as follows: Weight Gain equals $0.359 + 0.665t - 0.00106t^2$ wherein t is elapsed time in minutes. The rate of water flux at any time will be equal to the slope of the line, that is given by the following equation:

$$dy/dt = d(0.359 + 0.665t - 0.00106t^2)/dt$$

$$dy/dt = 0.665 - 0.00212t$$

To determine the initial rate of water flux the derivative is evaluated at $t = 0$, and $dy/dt = 0.665$ μl/min, which is equal to the coefficient b. Then, normalizing the imbition rate for timen, membrane surface area and thickness, the membrabe permeability constant to water, K, may be determined according to the following equation:

$$K\pi = 0.665 \ \mu l/min \times (60 \ min/hr) \times (1 \ ml/1000 \ \mu l)(0.008 \ cm/2.86 \ cm^2)$$

with $K = 1.13 \times 10^{-4}$ cm$^2$/hr. The value for NaCl was determined with a Hewlett-Packard vapor pressure osmometer to be 345 atm + 10% and, the K value for cellulose acetate used in this experiment calculated from NaCl imbibition values to be $1.9 \times 10^{-7}$ cm$^2$/hr atm.

Substituting into the calculated $K\pi$ expression $(1.9 \times 10^{-7}/cm^2/hr.atm)(\pi) = 1.13 \times 10^{-4}$ cm$^2$/hr, $\pi = 600$ atm at $t = 0$. As a method for evaluating the efficiency of a polymer with respect to duration of zero-order driving force, the % of water uptake was selected before the water flux values decreased to 90% of their initial values. The value of the initial slope for the equation of a straight line emanating from the % weight gained axis will be equal to the initial value of dy/dt evaluated at $t = 0$, with the y intercept c defining the linear swelling time, with $(dy/dt)0 = 0.665$ and the y intercept $= 0.359$, which yields $y = 0.665t + 0.359$. In order to determine when the value of the cumulative water uptake is 90% below the initial rate, the following expression is solved for t, $$0.9 = (at^2 + bt + c)/(bt + c) = (\Delta w/w)0.9$$

$$(-0.00106 \ t^2 + 0.665t + 0.359)/(0.665t + 0.359) = 0.9,$$

and solving for t, $$-0.00106t^2 + 0.0665t + 0.0359 = 0$$

$$t = (-0.0665 \pm [(0.0665)^2 - 4(-0.00106)(0.0359)]^{\frac{1}{2}})/2(-0.00106)$$

Figure 5:
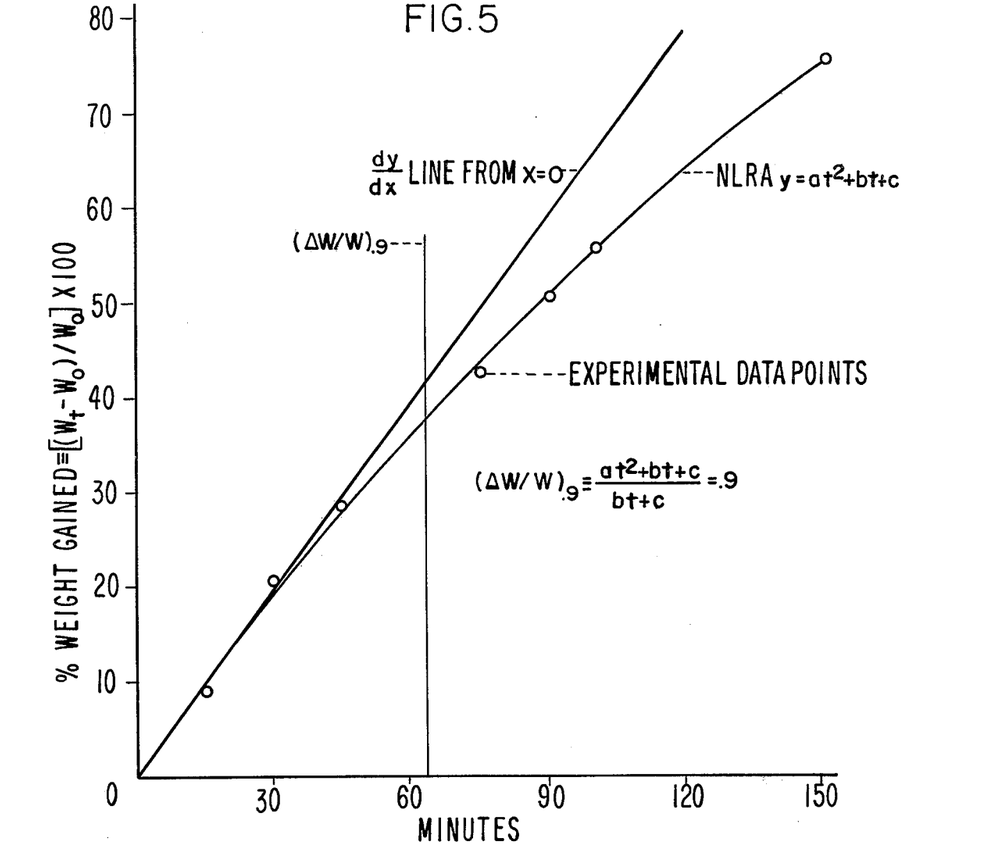
FIG. 5 represents the cummulative weight gain, as a function of time, of a polymer disc enclosed in a semipermeable membrane when the disc is submersed in water; and, FIG. 6 is graph depicting the cumulative rate of release of a beneficial agent from a device provided by the invention.
Figure 6:
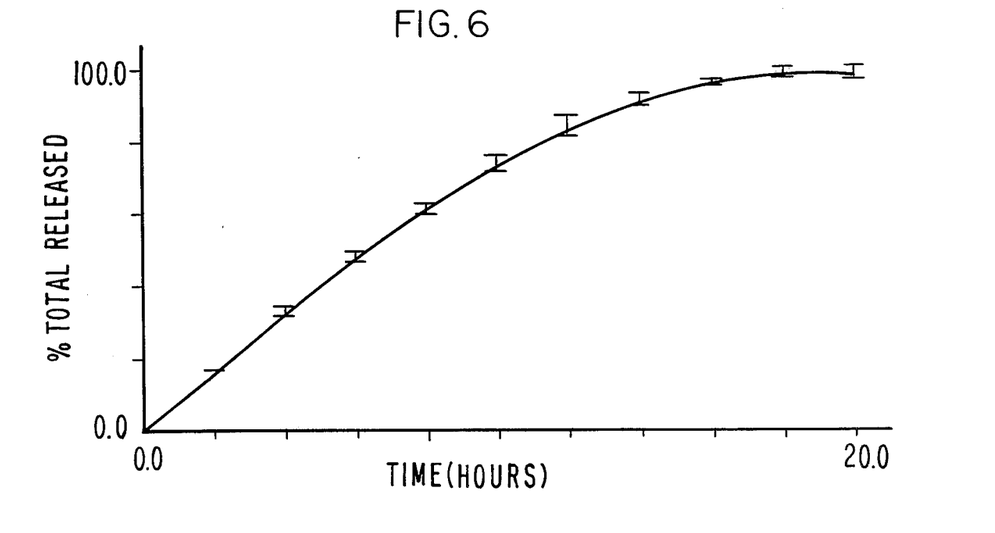

$t = 62$ min and the weight gain is $-0.00106(62)^2 + (0.665)(62) + 0.359 = 38$ μl, with the initial sample weight = 100 mg, thus $(\Delta w/w) \cdot 9 \times 100 = 38\%$. The results are presented in FIG. 5 for a graphical representation of the values. Other methods available for studying the hydrogel solution interface include rheologic analysis, viscometric analysis, ellipsometry, contact angle measurements, electrokinetic determinations, infrared spectroscopy, optical microscopy, interface morphology and microscopic examination of an operative device.

The device of the invention is manufactured by standard techniques. For example, in one embodiment, the agent and other ingredients that may be housed in one area of the compartment adjacent to the passageway, are pressed into a solid possessing dimension that corresponds to the internal dimensions of the area of the compartment the agent will occupy, or the agent and other ingredients and a solvent are mixed into a solid or semisolid form by conventional methods such as baelmilling, calendering, stirring or rollmilling, and then pressed into a preselected shape. Next, a layer of a hydrogel is placed on contact with the layer of agent in a like manner, and the two layers surrounded with a semipermeable wall. The layering of agent formulation and hydrogel can be fabricated by conventional two-layer press techniques. The wall can be applied by molding, spraying or dipping the pressed shapes into a wall forming material. Another and presently preferred technique that can be used for applying the wall is the air suspension procedure. This procedure consists in suspending and tumbling the pressed agent and dry hydrogel in a current of air and a wall forming composition until the wall is applied to the agenthydrogel composite. The air suspension procedure is described in U.S. Pat. No. 2,779,241; *J. Am. Pharm. Assoc.*, Vol. 48, pages 451 to 459, 1979; and ibid, Vol. 49, pages 82 to 84, 1960. Other standard manufacturing procedures are described in *Modern Plastics Encyclopedia*, Vol. 46, pages 62 to 70, 1969; and in *Pharmaceutical Sciences*, by Remington, Fourteenth Edition, pages 1626 to 1678, 1970, published by Mack Publishing Company, Easton, Penna.

Exemplary solvents suitable for manufacturing the wall include inorganic and organic solvents that do not adversely harm the wall forming material, and the final device. The solvents broadly include members selected from the group consisting of aqueous solvents, alcohols, ketones, esters, ethers, aliphatic hydrocarbons, halogenated solvents, cycloaliphatic, aromatics, heterocycyclic solvents, and mixtures thereof. Typical solvents include acetone, diacetone alcohol, methanol, ethanol, isopropyl alcohol, butyl alcohol, methyl acetate, ethyl acetate, isopropyl alcohol, butyle alcohol, methyl acetate, ethyl acetate, isopropyl acetate, n-butyl acetate, methyl isobutyl ketone, methyl propyl ketone, n-hexane, n-heptane, ethylene glycol monoethyl ether, ethelene glycol monoethyl acetate, methylene dichloride, ethylene dichloride, propylene dichloride, carbon tetrachloride, nitroethane, nitropropane, tetrachloroethane, ethyl ether, isopropyl ether, cyclohexane, cyclo-octane, benzene toluene, naphtha, 1,4-dioxane, tetrahydrofuran, diglyme, water, and mixtures thereof such as acetone and water, acetone and methanol, acetone and ethyl alcohol, methylene dichloride and methanol, and ethylene dichloride and methanol, and mixtures thereof.

The expression "passageway" as used herein comprises means and methods suitable for releasing the agent from the system. The expression includes aperture, orifice or bore through wall 12 formed by mechanical procedures, or by eroding an erodible element, such as gelatin plug, in the environment of use. A detailed description of osmotic passageways and the maximum and minimum dimensions for a passageway are disclosed in U.S. Pat. Nos. 3,845,770 and 3,916,899.

DESCRIPTION OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

An osmotic therapeutic device for the controlled and continuous oral release of the beneficial drug oxprenolol hydrochloride was made as follows: 249.24 mg of oxprenolol hydrochloride, 10.72 mg of polyvinyl pyrrolidone, and 8.0 mg of magnesium stearate are mixed thoroughly and pressed in a Manesty press with a 7/16 inch punch using a pressure head of 1½ tons to produce a layer of the drug composition. Next, 300 mg of polyacrylamide, sold under the name of Cyanamer ® A-370, a hydrogel polymer of approximately 200,000 mol. wt. was added to the Manesty press and pressed to form a layer of hydrogel in contact with the layer of drug.

Next, a semipermeable wall was formed by blending 170 g of cellulose acetate having an acetyl content of 39.8 with 4 of methylene chloride and 400 ml of methanol, and spray coating the two layered compartment forming member in an air suspension machine having a 1.8 kg charge until a 5.1 mil thick semipermeable wall surrounds the compartment. The coated device was dried for 72 hours at 50° C., and then a 15 mil passageway was laser drilled through the semipermeable wall to connect the layer of drug with the exterior of the device. Accompanying FIG. 4 dipicts the cummulative amount of drug released by the device over a prolonged period of time.

EXAMPLE 2

The procedure of Example 1 is repeated in this example will all conditions as previously described except that the drug in the compartment is replaced with a member selected from the group consisting of hypnotics, sedative, psychic energizers, tranquilizers, anticonvulsants, muscle relaxants, antiparkinson drugs, analgesics, anti-inflammatory, anesthelics, muscle contractants, anti-microbials, antimalarials, hormones, sympathomimetic and diuretics.

EXAMPLE 3

The procedures of Examples 1 and 2 are repeated in this example, with all conditions as described except that the drug in the compartment is replaced with a member selected from the group consisting of prochlorperazine edisylate, ferrous sulfate, aminocaprioc acid, potassium chloride, mecamylamine, hydrochloride, amphetamine sulfate, benzphetamine hydrochloride, isproternol sulfate, methamphetamine hydrochloride, phenmetrazine hydrochloride, bethanechol chloride, methacholine chloride, atropine sulfate, methscopolamine bromide, isopropamide iodide, tridihexethyl chloride, phenformin hydrochloride, and methylpehnidate hydrochloride.

EXAMPLE 4

An osmotic therapeutric device manufactured in the form of an oral delivery device for delivering oxtriphylline to the gastrointestional tract was manufactured as follows: first a 450 mg composition comprising 95% oxtriphylline, 4% polyvinyl pyrrolidone and 1% magnesium stearate was prepared by blending the three ingredients into a homogenous blend, and then pressed into a solid mass in a commercially available Manesty tableting machine set to a Stoke's hardness of 8 kg. Next, 60 mg of lightly cross-linked polyethylene oxide was added to the tableting machine and pressed into a solid mass in contact with the drug. Then, the two layered mass was coated in a standard air suspension machine with a semipermeable polymeric wall formed from a 5% solution consisting of cellulose acetate having an acetyl content of 38.3%, in a solvent consisting of acetone and water, 95:5, wt to wt. Finally, an osmotic passageway having a diameter of 10 mils was drilled through the wall facing the oxtriphyline for delivering it from the device. The semipermeable wall of the device was 7.1 mils thick.

EXAMPLE 5

An osmotic therapeutic device manufactured in the form of an oral osmotic device for delivering indomethacin was manufactured by following the procedure of Example 4, with all conditions and procedures as described, except in this example the layer of drug formulation weight 215 mg and comprised 48% sodium indomethacin, 48% osmagent mannitol and 4% candelilla, the hydrogel layer weight 80 mg and comprised lightly cross-linked polyoxyethylene, the semipermeable wall was 5 mils thick comprising 88% cellulose acetate having an acetyl content of 32% and 12% sorbitol, formed from a solvent consisting essentially of 360 ml of water and 3,470 ml of acetone, and a passageway with a diameter of 8.1 mils.

EXAMPLE 6

The procedure of Examples 4 and 5 are repeated in this example with all conditions as described except that the device is designed as an ocular osmotic insert and the layer of drug in the compartment is an ophthalmic drug that is a member selected from the group consisting of idoxuridine, phenylephrine, pilocarpine hydrochloride, eserine, carbachol, phospholine iodine, demecarium bromide, cyclopentolate, homatropine, scopolamine, and epinephrine.

The novel osmotic systems of this invention use means for the obtainment of precise release rates in the environment of use while simultaneously maintaining the integrity and character of the system. While there has been described and pointed out features of the invention as applied to presently preferred embodiments, those skilled in the art will appreciate that various modifications, changes, additions and omissions in the systems illustrated and described can be made without departing from the spirit of the invention.

We claim:

1. An osmotic device for the controlled delivery of a beneficial agent to a fluid environment of use, comprising:
   a. a wall formed of a semipermeable material permeable to the passage of an exterior aqueous fluid present in environment of use and substantially impermeable to the passage of beneficial agent, the semipermeable wall surrounding and forming;
   b. a compartment containing a layer of beneficial agent, that is insoluble to very soluble in the aqueous fluid and a layer of an expandable hydrogel; and,
   c. a passageway in the semipermeable wall communicating with the layer of beneficial agent in the compartment and with the exterior of the device.

2. The osmotic device for the controlled delivery of the beneficial agent according to claim 1 wherein the layer of beneficial agent contains an osmagent.

3. The osmotic device for the controlled delivery of the benficial agent according to claim 1 wherein the wall is formed of a member selected from the group consisting of cellulose acylate, cellulose diacylate, cellulose triacylate, cellulose acetate, cellulose diacetate and cellulose triacetate.

4. The osmotic device for the controlled delivery of the benificial agent according to claim 1 wherein the agent is a member selected from the group consisting of pesticides, herbicides, germicides, fungicides, insecticides and algicides.

5. The osmotic device for the controlled delivery of agent according to claim 1 wherein the hydrogel is cross-linked.

6. The osmotic device for the controlled delivery of agent according to claim 1 wherein layer of agent contains osmagent and suspending agent.

7. An osmotic device for the controlled delivery of a beneficial drug to a biological environment of use, comprising:
   a. a shaped wall formed of a semipermeable material permeable to the passage of an exterior fluid present in the environment of use, and substanitially impermeable to the passage of drug, the wall surrounding and forming:
   b. a compartment comprising a drug that is soluble to very soluble in the biological fluid and exhibits an osmotic pressure gradient across the wall against the exterior fluid, and a layer of an expandable hydrogel in contact with the drug formation, which hydrogel can expand from a rested to an expanded state in the presence of exterior fluid imbibed into the compartment; and,
   c. a passageway in the wall communicating with the exterior of the device and the drug for delivering the drug formulation from the device at a controlled rate over a prolonged period of time.

8. The osmotic device for the controlled delivery of the beneficial drug according to claim 7, wherein the device when in operation in the environment of use, imbides fluid through the wall into the compartment, thereby (1) producing a solution of drug, and (2) causing the hydrogel to expand, whereby through the combined operation of (1) and (2) the solution is delivered through the passageway from the compartment to the exterior of the device over time 9. The osmotic device for the controlled delivery of the drug according to claim 7 wherein drug is mixed with an osmagent that is soluble in the biological fluid and exhibits an osmotic pressure gradient across the semipermeable wall against the exterior fluid.

10. The osmotic device for the controlled delivery of the drug formulation according to claim 7 wherein the drug is present in the compartment as a layer thereof.

11. The osmotic device for the controlled delivery of the drug according to claim 7 wherein the biological environment of use is the gastrointestinal tract.

12. The osmotic device for the controlled delivery of the drug according to claim 7 wherein the biological environment of use is the vaginal channel.

13. The osmotic device for delivering the drug according to claim 7 wherein the hydrogel is cross-linked.

14. The osmotic device for delivering the drug according to claim 7 wherein the drug is mixed with a suspending agent.

15. The osmotic device for the controlled delivery of the drug according to claim 7 wherein the biological environment of use is the ano-rectal canal.

16. The osmotic device for the controlled delivery of the drug according to claim 7 wherein the drug is a member selected from the group consisting essentially of metoprolol, diclofenac, oxprenolol, hydralazine, aspirin, levodopa, valproate, and theophylline.

17. The osmotic device for the controlled delivery of the drug according to claim 7 wherein the environment of use is a human.

18. The osmotic device for the controlled delivery of the drug according to claim 7 wherein the drug is a member selected from the group consisting essentially of central nervous system, depressant, hypnotic, sedative, psychic energizer, tranquilizer, anticonvulsant, muscle relaxant, antiparkinson, analgesic, antiinflammatory, anesthetic, muscle contractant, hormonal, contraceptive, sympathomimetic, diuretic, cardiovascular, hypoglycemic, and ophthalmic drugs.

19. An osmotic device for the controlled delivery of a beneficial drug formulation to a biological environment of use, comprising:
   a. a shaped semipermeable wall permeable to the passage of an exterior biological fluid and substantially impermeable to the passage of drug formulation, the wall surrounding and forming;
   b. a compartment comprising a drug formulation, which formulation comprises a drug that is insoluble to poorly soluble in the biological fluid and an osmotically effective solute that is soluble in the exterior fluid and exhibits an osmotic pressure gradient across the wall against the fluid, and a layer of a hydrogel in contact with the drug formulation, which hydrogel can absorb fluid that enters the compartment and swell; and,
   c. a passageway in the semipermeable wall connecting the exterior of the device and drug formulation for delivering the drug formulation from the device to the environment at a controlled rate over a prolonged period of time.

20. The osmotic device for the controlled delivery of the beneficial drug formulation according to claim 17 wherein the environment of use is a human.

21. The osmotic device for the controlled delivery of the beneficial drug formulation according to claim 17 wherein the environment of use is the gastrointestinal tract and the device is sized and shaped for oral admittance therein.

22. The osmotic device for the controlled delivery of the beneficial drug formulation according to claim 17 wherein the environment of use is the vagina and the device is adapted for placement and retention therein.

23. The osmotic device for the controlled delivery of the beneficial drug formulation according to claim 17 wherein the environment of use is the ano-rectal canal and the device is adapted for insertion therein.

24. The osmotic device for the controlled delivery of the beneficial drug formulation according to claim 17, wherein when fluid is imbibed into the compartment, the hydrogel interacts with the fluid and retains the fluid within its hydrogel structure without dissolution, and exhibits a 2 to 50 fold increase in volume.

25. The osmotic device for the controlled delivery of the beneficial drug formulation according to claim 17, wherein when fluid is imbibed into the compartment, a precipitate is formed in the surface of the hydrogel at the interface defined by the hydrogel and the drug formulation.

26. The osmotic device for the controlled delivery of the drug according to claim 17 wherein the drug is mixed with a suspending agent.

27. The osmotic device for the controlled delivery of the beneficial drug formulation according to claim 19, wherein when fluid is imbibed into the compartment, a precipitate is formed in the surface of the hydrogel at the interface defined by the hydrogel and the drug formulation.

28. The osmotic device for the controlled delivery of the beneficial agent according to claim 1 wherein the agent is the drug phenoxybenzamine.

29. The osmotic device for the controlled delivery of the beneficial agent according to claim 1 wherein the agent is the drug norgestrel.

30. The osmotic device for the controlled delivery of the beneficial agent according to claim 1 wherein the agent is the drug norethindone.

31. The osmotic device for the controlled delivery of the beneficial agent according to claim 1 wherein the agent is the drug norethynodrel.

32. The osmotic device for the controlled delivery of the beneficial agent according to claim 1 wherein the agent is the drug norgesterone.

33. The osmotic device for the controlled delivery of the beneficial agent according to claim 1 wherein the agent is the drug norethisterone.

34. The osmotic device for the controlled delivery of the beneficial agent according to claim 1 wherein the agent is the drug progesterone.

35. The osmotic device for the controlled delivery of the beneficial agent according to claim 1 wherein the agent is the drug metaprolol.

36. The osmotic device for the controlled delivery of the beneficial agent according to claim 1 wherein the agent is the drug diclofenac.

37. The osmotic device for the controlled delivery of the beneficial agent according to claim 1 wherein the agent is the drug indomethacin.

38. The osmotic device for the controlled delivery of the beneficial agent according to claim 1 wherein the agent is the drug oxprenolol.

39. The osmotic device for the controlled delivery of the beneficial agent according to claim 1 wherein the agent is the drug l-dopa.

40. The osmotic device for the controlled delivery of the beneficial agent according to claim 1 wherein the agent is the drug valporate.

* * * * *